US00PP32502P2

(12) United States Plant Patent
Wood

(10) Patent No.: US PP32,502 P2
(45) Date of Patent: Nov. 24, 2020

(54) ***RHAMNUS* PLANT NAMED 'SMNRFBL'**

(50) Latin Name: *Rhamnus frangula*
Varietal Denomination: SMNRFBL

(71) Applicant: Spring Meadow Nursery, Inc., Grand Haven, MI (US)

(72) Inventor: Timothy D Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,603

(22) Filed: Nov. 5, 2019

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct *Rhamnus* cultivar named 'SMNRFBL' is disclosed, characterized by wide, dense foliage. Plants are vigorous and full, with good basal branching forming dense plants to the base. The new variety is a *Rhamnus*, normally used for outdoor ornamental purposes.

1 Drawing Sheet

Latin name of the genus and species: *Rhamnus frangula*. Variety denomination: 'SMNRFBL'.

BACKGROUND OF THE INVENTION

The new *Rhamnus* cultivar is a product of a naturally-occurring whole plant mutation discovered by the inventor, Timothy Wood, in Grand Haven, Mich. The parent is the commercial variety *Rhamnus* 'Ron Williams', U.S. Plant Pat. No. 14,791.

The new variety was found and selected in Spring of 2016 by the inventor in a group of seedlings in a nursery in Grand Haven, Mich.

Asexual reproduction of the new cultivar has been performed by softwood cuttings. This was first performed at the same nursery in Grand Haven, Mich. in Spring 2016, and has shown that the unique features of this cultivar are stable and reproduced true to type in multiple successive generations.

SUMMARY OF THE INVENTION

The cultivar 'SMNRFBL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNRFBL' These characteristics in combination distinguish 'SMNRFBL' as a new and distinct *Rhamnus* cultivar:

1. Wide foliage.
2. Dense foliage.
3. Full plant to the base.

PARENT COMPARISON

Plants of the new cultivar 'SMNRFBL' are similar to plants of the parent in most horticultural characteristics; however, plants of the new cultivar 'SMNRFBL' differ in the following;

1. The new variety has wider leaves than the parent.
2. The new variety is a denser plant than the parent.
3. The new variety produces leaves to the base of the plant, while the parent does not, and is bare towards the bottom of the plant.

COMMERCIAL COMPARISON

Plants of the new cultivar 'SMNRFBL' are comparable to a *Rhamnus* 'SMNRFBT', co-pending and having application Ser. No. 16/602,606. The two *Rhamnus* varieties are similar in most horticultural characteristics; however, the new variety 'SMNRFBL' differs in the following;

1. The new variety has wider leaves than this comparator.

BRIEF DESCRIPTION OF THE PHOTOGRAPH

The accompanying photograph illustrates in full color a typical plant of 'SMNRFBL' in a 2 gallon pot. Age of the plant photographed is approximately 2-3 years old from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNRFBL' plants grown in a poly greenhouse during May of 2019, in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Rhamnus frangula* 'SMNRFBL'.

PROPAGATION

Type of propagation typically used: Softwood cuttings.
Time to initiate roots: 12 days in Summer.
Time to produce a rooted cutting: 3 months in Summer.
Root description: Thin to thick, fibrous, moderately dense, freely branching. Tan to brown in color, not accurately measured with R.H.S. Chart.

PLANT

Plant type: Perennial deciduous shrub.
Age of plant described: 2 years old from a rooted cutting.
Container size: 3 gallon container.
Overall plant shape: Very upright, columnar.
Growth habit: Upright.
Plant spread: 47 cm.
Plant height: 64 cm.
Plant vigor: Strong, vigorous.
Branching habit: Freely branching from the base.
Length of primary lateral branches: 45.5 cm.
Diameter of lateral branches: 5 mm.
Quantity of lateral branches: Approximately 25.
Stem:
*Color*.—RHS Brown N200A; new growth Green 143B.
*Shape*.—Round.
*Strength*.—Strong.
*Aspect angle*.—0-15° from vertical.
*Pubescence*.—No.
*Lenticel color*.—RHS Greyed-Orange 164D.
Internode length: 1.5 cm.

FOLIAGE

Leaf:
*Arrangement*.—Alternate, single.
*Average length*.—11 cm.
*Average width*.—15 to 25 mm.
*Shape of blade*.—Elliptic to narrow elliptic.
*Apex*.—Acute.
*Base*.—Cuneate.
*Margin*.—Sparse irregular crenations, undulate.
*Texture of top surface*.—Glabrous, smooth.
*Texture of bottom surface*.—Glabrous, smooth.
*Color*.—Young foliage in Spring upper side: RHS Yellow-Green 144A. Young foliage in Spring under side: RHS Yellow-Green 144A. Mature foliage upper side: RHS Green 138A. Mature foliage under side: RHS Green 138B. Fall foliage upper side: Near RHS Yellow 7B. Fall foliage under side: Near RHS Yellow 7C.
*Venation*.—Type: Pinnate. Venation color upper side: RHS Yellow-Green 151B. Venation color under side: RHS Yellow-Green 145C.
*Petiole*.—Length: 1 cm. Diameter: 1 mm. Texture, upper side: Some pubescence. Texture, under side: Some pubescence. Color, upper side: RHS Yellow-Green 144C. Color, under side: RHS Yellow-Green 144C.

FLOWER

Not observed to date.

REPRODUCTIVE ORGANS

Not observed.

OTHER CHARACTERISTICS

Fruits and seeds: Not observed to date.
Disease/pest resistance: Neither resistance nor susceptibility to normal diseases and pests of *Rhamnus* observed.
Temperature range: Observed to tolerate a temperature range from −28° C. to 35° C. Root hardy to −28C, top of the plant does die back to the ground.

What is claimed is:

1. A new and distinct cultivar of *Rhamnus* plant named 'SMNRFBL' as herein illustrated and described.

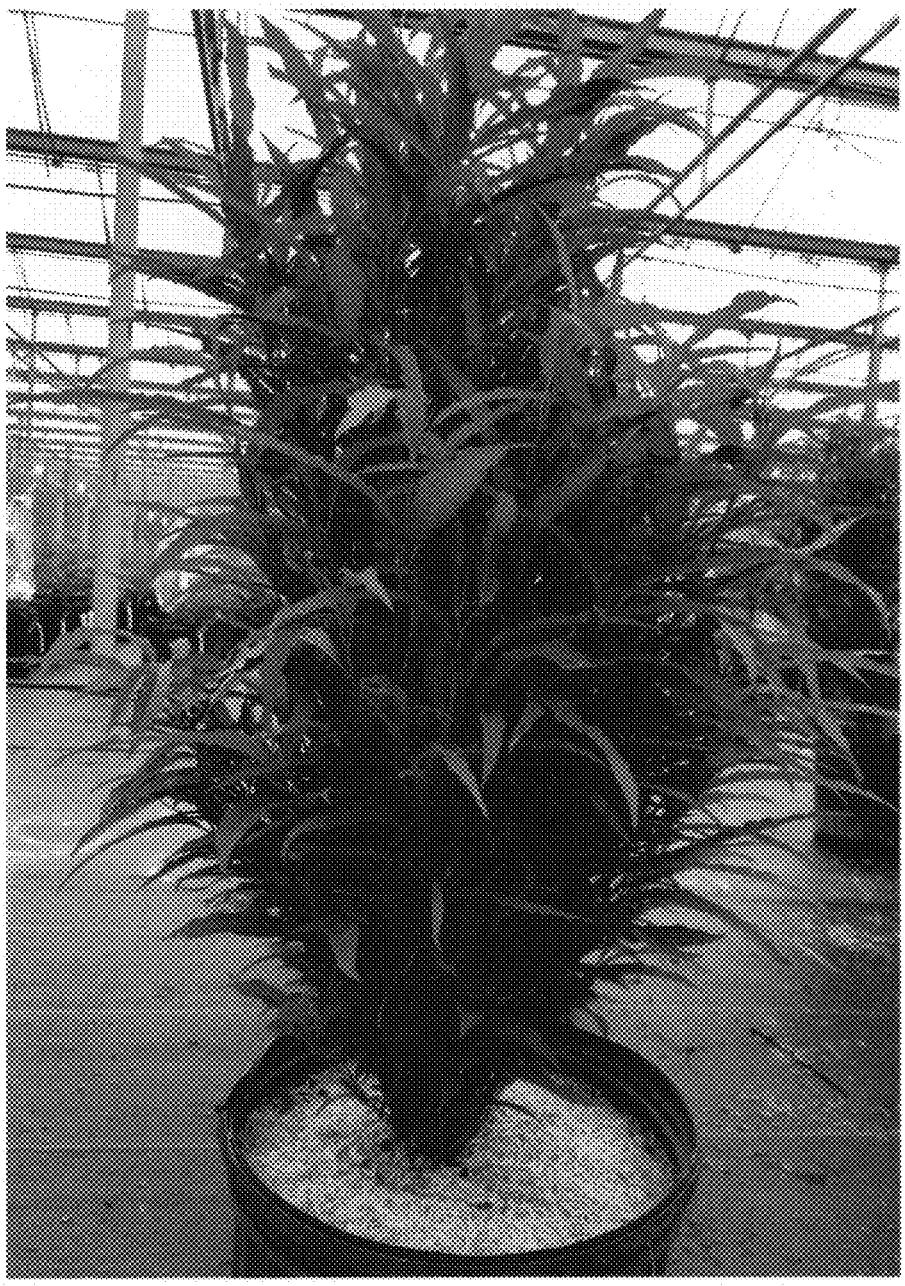

* * * * *